US012593995B2

United States Patent

(10) Patent No.: US 12,593,995 B2

(12) United States Patent
Liu

(45) Date of Patent: Apr. 7, 2026

(54) BLOOD PRESSURE MEASURING DEVICE

(71) Applicant: GOERTEK INC., Weifang (CN)

(72) Inventor: Chao Liu, Weifang (CN)

(73) Assignee: GOERTEK INC., Weifang (CN)

( * ) Notice: Subject to any disclaimer, the term of this patent is extended or adjusted under 35 U.S.C. 154(b) by 545 days.

(21) Appl. No.: 18/006,155

(22) PCT Filed: Nov. 5, 2020

(86) PCT No.: PCT/CN2020/126639
§ 371 (c)(1),
(2) Date: Jan. 20, 2023

(87) PCT Pub. No.: WO2022/016739
PCT Pub. Date: Jan. 27, 2022

(65) Prior Publication Data

US 2023/0284919 A1     Sep. 14, 2023

(30) Foreign Application Priority Data

Jul. 22, 2020    (CN) .......................... 202010727633.8

(51) Int. Cl.
*A61B 5/022*        (2006.01)
*A61B 5/00*        (2006.01)
(52) U.S. Cl.
CPC ............ *A61B 5/022* (2013.01); *A61B 5/0053* (2013.01); *A61B 5/681* (2013.01)
(58) Field of Classification Search
None
See application file for complete search history.

(56) References Cited

U.S. PATENT DOCUMENTS 4,938,226 A   *   7/1990   Danielsson  ........  A61B 5/02208
                                                            600/492
2001/0005777 A1      6/2001   Nakagawa et al.
                    (Continued)

FOREIGN PATENT DOCUMENTS

CN          202313298 U        7/2012
CN          204909424 U       12/2015
                    (Continued)

OTHER PUBLICATIONS

International Search Report from International Application No. PCT/CN2020/126639 mailed Apr. 21, 2021.

*Primary Examiner* — Aurelie H Tu
(74) *Attorney, Agent, or Firm* — Shih IP Law Group, PLLC

(57)           ABSTRACT

A blood pressure measuring device comprises a device body, an air bag, an air nozzle and a piston, an air pump is provided in the device body, a casing of the device body is provided with a mounting hole and an air channel connection hole communicating with the mounting hole, the air channel connection hole is communicated with an air outlet of the air pump, the piston is installed in the mounting hole, the piston includes a piston sealing portion capable of forming a seal with the mounting hole positioned above the air channel connection hole, the air nozzle includes a through hole communicating with the air bag, when the air nozzle is inserted into the mounting hole, the air nozzle presses the piston downward until the piston sealing portion is positioned below the air channel connection hole, the through hole is communicated with the air channel connection hole.

9 Claims, 5 Drawing Sheets

(56)                    References Cited

U.S. PATENT DOCUMENTS

| | | |
|---|---|---|
| 2009/0124911 A1 | 5/2009 | Lin et al. |
| 2019/0125200 A1* | 5/2019 | Karla ................. A61B 5/02141 |
| 2020/0085319 A1* | 3/2020 | Lin ......................... F04B 53/10 |

FOREIGN PATENT DOCUMENTS

| | | |
|---|---|---|
| CN | 106419882 A | 2/2017 |
| CN | 107080532 A | 8/2017 |
| CN | 108378836 A | 8/2018 |
| CN | 109700444 A | 5/2019 |
| CN | 110327027 A | 10/2019 |
| CN | 110638155 A | 1/2020 |
| CN | 110897282 A | 3/2020 |
| CN | 11820882 A | 10/2020 |
| JP | 2000051158 A | 2/2000 |

* cited by examiner

BLOOD PRESSURE MEASURING DEVICE

The present application claims the priority of the Chinese Patent Application No. 202010727633.8, titled "a blood pressure measuring device" filed in China Patent Office on Jul. 22, 2020, the entire contents of which are incorporated into the present application by reference.

TECHNICAL FIELD

The present application relates to a technical field of blood pressure measurement, and more particularly, to a blood pressure measuring device.

DESCRIPTION OF RELATED ART

At present, sphygmomanometers and wearable products with blood pressure measurement function on the market, such as watches and wristbands with blood pressure monitoring function, perform blood pressure detection generally by sensors and by driving air bags with air pumps. Since an air nozzle is required to be disposed for the connection of an airbag, and it is difficult for the waterproofing of the air nozzle at a connection port, common blood pressure measurement device generally does not have a waterproof function, which limits its use in special environments such as underwater and a humid environment.

Based on above, it is a problem needed to be solved by those skilled in the art at present about how to effectively solve the problem of limited use of blood pressure measurement device in special environments such as underwater and a humid environment.

SUMMARY

In view of the above, a purpose of the present application is to provide a blood pressure measuring device, the design of the structure of the blood pressure measuring device can effectively solve the problem of the limited use of the blood pressure measuring device in special environments such as underwater and a humid environment.

In order to achieve the above purpose, the present application provides the following technical solutions:

A blood pressure measuring device, comprising a device body, an air bag, an air nozzle and a piston, wherein an air pump is provided in the device body, a mounting hole and an air passage connection hole communicating with the mounting hole are provided on a casing of the device body, and the air passage connection hole is communicated with an air outlet of the air pump, wherein the piston is installed in the mounting hole, and the piston includes a piston sealing portion to form a seal between the piston sealing portion and the mounting hole positioned above the air passage connection hole, and wherein the air nozzle includes a through hole communicating with the air bag, when the air nozzle is inserted into the mounting hole, the air nozzle presses the piston downward until the piston sealing portion is positioned below the air passage connection hole, and the through hole is communicated with the air passage connection hole.

Preferably, in the blood pressure measuring device, a bottom end of the piston is provided with a hook, and a side wall of the mounting hole is provided with a stopper cooperating with the hook, to lock the piston sealing portion of the piston above the air passage connection hole.

Preferably, in the blood pressure measuring device, the mounting hole is a stepped hole including an upper hole and a lower hole with an inner diameter larger than that of the upper hole, the air passage connection hole is communicated with the lower hole, and the stopper cooperating with the hook is formed between the upper hole and the lower hole.

Preferably, in the blood pressure measuring device, a top end of the piston is formed with a protrusion, and when the air nozzle presses the piston downward, a lower end surface of the air nozzle abuts against the protrusion to form a connection channel communicating with the through hole, allowing gas to flow therethrough between the piston and the air nozzle.

Preferably, in the blood pressure measuring device, the piston sealing portion is a sealing ring provided on an outer wall surface of the piston, and a seal is formed between the sealing ring and a side wall of the mounting hole.

Preferably, in the blood pressure measuring device, further comprises a restoring elastic member cooperating with the piston, and the restoring elastic member deforms when the piston moves downward relative to the mounting hole, so as to generate a force that pushes the piston to restore to an upper portion of the mounting hole.

Preferably, in the blood pressure measuring device, the restoring elastic member is a compression spring having opposite ends abutting against bottom surfaces of the piston and the mounting hole, respectively.

Preferably, in the blood pressure measuring device, the casing is further provided with a vent hole having one end communicating with the mounting hole and the other end communicating with an outside of the casing, and a pressure relief hole having one end communicating with the mounting hole and the other end communicating with an air inlet of the air pump, the vent hole isolates from the pressure relief hole when the piston sealing portion of the piston is positioned above the air passage connection hole, and the vent hole is communicated with the pressure relief hole when the air nozzle presses the piston downward.

Preferably, in the blood pressure measuring device, the vent hole, the pressure relief hole and the air passage connection hole are disposed sequentially from top to bottom along an axial direction of the mounting hole, wherein the piston seals the an upper portion of the pressure relief hole in the mounting hole, and wherein the air nozzle comprises an air nozzle sealing portion having a bottom end for sealing the side wall of the mounting hole, and an annular ventilation groove positioned above the air nozzle sealing portion and communicating with the vent hole, a side of the vent groove facing the pressure relief hole extends downward to form a communication groove communicating with the pressure relief hole.

The blood pressure measuring device according to the present application includes a device body, an air bag, an air nozzle and a piston, wherein the device body includes a casing, an air pump is provided in the device body, and a mounting hole and an air passage connection hole communicating with the mounting hole are provided on the casing, and the air passage connection hole is communicated with an air outlet of the air pump, wherein the piston is installed in the mounting hole, and the piston includes a piston sealing portion capable of forming a seal between the piston and the mounting hole positioned above the air passage connection hole, and wherein the air nozzle can be inserted into the mounting hole, and when the air nozzle is inserted into the mounting hole, the air nozzle presses the piston downward, such that the piston sealing portion is positioned below the air passage connection hole, and wherein the air nozzle includes a through hole having one end for communicating with the air bag and the other end communicating with the air passage connection hole when the air nozzle presses the piston downward until the piston sealing portion is positioned below the air passage connection hole.

According to the blood pressure measuring device of the present application, if the blood pressure measurement is not performed, it is not necessary to connect the air nozzle and the air bag, and the piston is installed on the upper portion of the mounting hole, that is, a seal is formed between the piston sealing portion of the piston and the mounting hole positioned above the air passage connection hole, thereby achieving a seal between the inside and the outside of the casing, preventing external water from entering inside the casing, and thus achieving the purpose of waterproofing. If the blood pressure needs to be measured, the air nozzle is pressed into the mounting hole, and the air nozzle pushes the piston moving downward, so that the piston sealing portion is positioned below the air passage connection hole, and thus the through hole of the air nozzle communicates with the air passage connection hole, thereby achieving the communication between the air outlet of the air pump and the air bag, for achieving the blood pressure measurement. In conclusion, according to the blood pressure measuring device of the present application, by the up and down movement of the piston in the mounting hole and the cooperation of the piston and the air passage connection hole, the device body can be waterproof when the airbag is removed in the case that the air bag is not used at ordinary times, and the air nozzle of the air bag is connected if blood pressure needs to be measured, so that the blood pressure thus can be measured normally.

BRIEF DESCRIPTION OF DRAWINGS

In order to more clearly illustrate the embodiments of the present application or the technical solutions in the prior art, the drawings required to be used for the content of the embodiments or the prior art will be briefly introduced in the following. Obviously, the drawings in the following description are merely a part of the drawings of the present application and for those of ordinary skill in the art, other drawings can also be obtained from the provided drawings without any creative effort.

Figure 1:
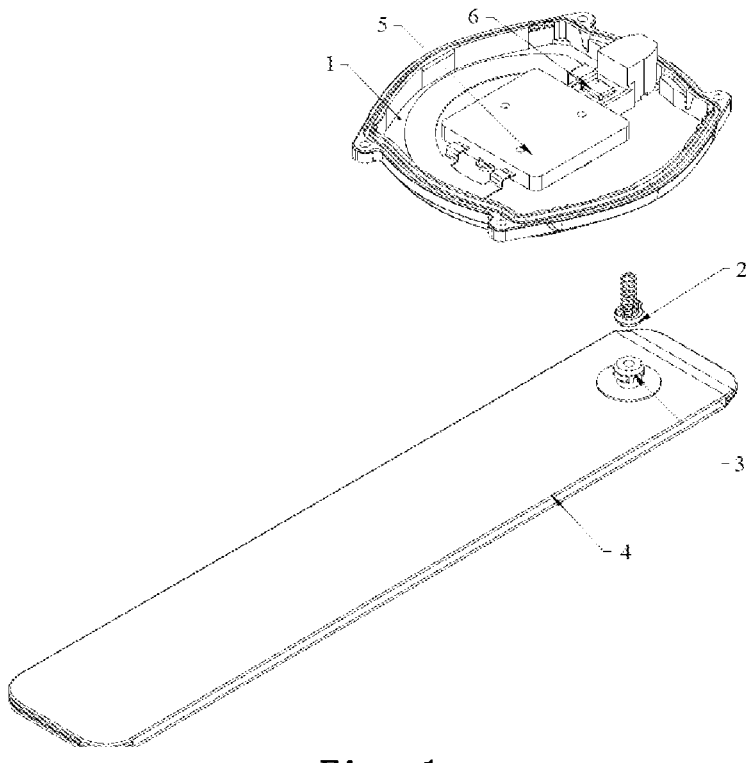
FIG. 1 is a partial exploded structural schematic front view of a blood pressure measuring device according to a detailed embodiment of the present application.

The reference numbers in the drawings are follows:

casing 1, piston 2, air nozzle 3, air bag 4, air pump 5, barometer 6, restoring elastic member 7, mounting hole 11, air passage connection hole 12, vent hole 13, pressure relief hole 14, air passage 15, hook 21, protrusion 22, sealing ring 23, air nozzle sealing portion 31, vent groove 32, communication groove 33, air nozzle clamp 34, through hole 35.

DETAILED DESCRIPTIONS

An embodiment of the present application discloses a blood pressure measuring device, which can be used in special environments such as underwater and humid environment.

Technical solutions of embodiments of the present application will be described below with reference to the drawings in the embodiments of the present application. Obviously, the described embodiments are only a part of the embodiments of the present application, rather than all the embodiments. Based on the embodiments in the present application, all other embodiments obtained by those of ordinary skill in the art without creative efforts shall fall within the protection scope of the present application.

Figure 2:
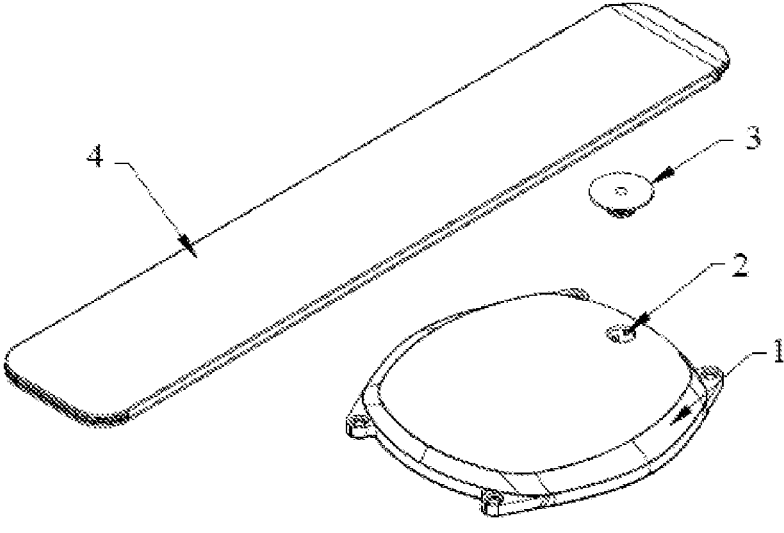
FIG. 2 is a back side schematic view corresponding to FIG. 1.
Figure 3:
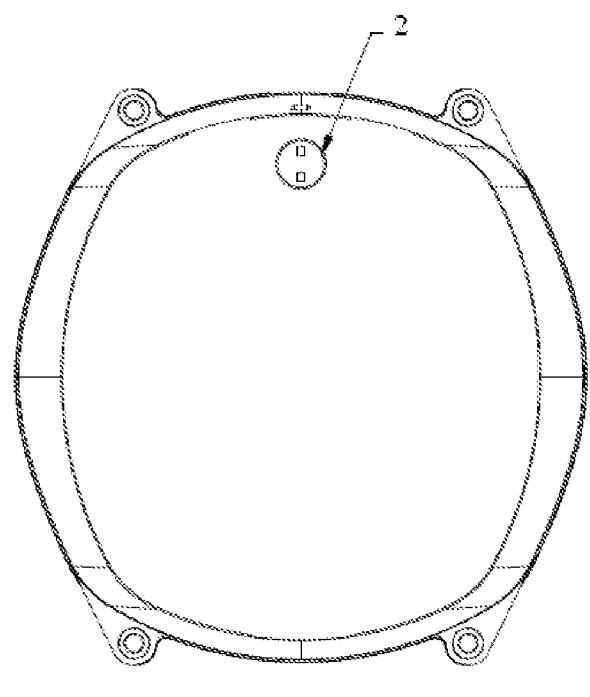
FIG. 3 is a schematic view of a casing in a state where an air nozzle is not pressed.
Figure 4:
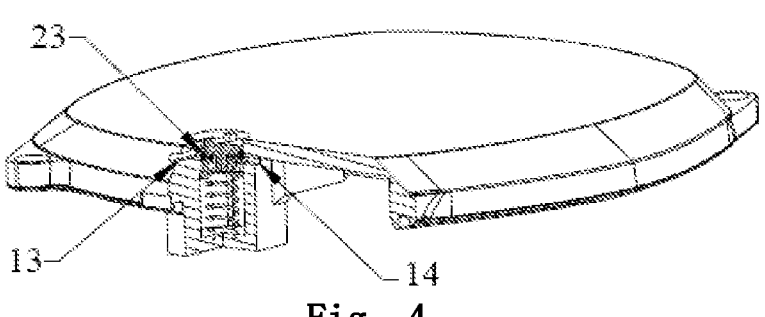
FIG. 4 is a partial sectional view of FIG. 3.

Referring to FIGS. 1 to 4. FIG. 1 is a partial exploded structural schematic front view of a blood pressure measuring device according to a detailed embodiment of the present application; FIG. 2 is a back side schematic view corresponding to FIG. 1; FIG. 3 is a schematic view of a casing in a state where an air nozzle is not pressed; and FIG. 4 is a partial sectional view of FIG. 3.

In a detailed embodiment, the blood pressure measuring device according to the present application includes a device body, an air bag 4, an air nozzle 3 and a piston 2.

Here, the device body includes a casing 1. An air pump 5 is provided in the casing 1, and a mounting hole 11 and an air passage connection hole 12 communicating with the mounting hole 11 are provided in the casing 1. The air passage connection hole 12 communicates with an air outlet of the air pump 5. The mounting hole 11 is used for installing the piston 2 and the air nozzle 3, and a shape of the mounting hole 11 is correspondingly provided according to shapes of the piston 2 and the air nozzle 3. Generally, the mounting hole 11 is a circular hole. One end of the air passage connection hole 12 is connected with the mounting hole 11, and the other end thereof is connected with the air outlet of the air pump 5. Specifically, an air passage 15 may be provided in the casing 1, and the air outlet of the air pump 5 communicates with the air passage 15. The air passage connection hole 12 communicates with the air outlet of air pump 5 by communicating with the air passage 15. For the detailed structure and function of the air pump 5, reference may be made to the relevant setting of the conventional air pump 5, which will not be repeated here.

The piston 2 is installed in the mounting hole 11, and the piston 2 includes a piston sealing portion. A seal may be formed between the piston sealing portion and the mounting hole 11 positioned above the air passage connection hole 12. The air nozzle 3 can be inserted into the mounting hole 11, and when the air nozzle 3 is inserted into the mounting hole 11, the piston 2 is pressed downward, so that the piston sealing portion is positioned below the air passage connection hole 12. That is, the piston 2 can not only be sealed in the mounting hole 11 but also can move down along the mounting hole 11 under an action of external force. It should be noted that the piston sealing portion refers to a portion of the piston 2 that can form a seal between the piston 2 and the mounting hole 11, and it may be a part of the piston 2 or the entire piston 2 according to the shape of the piston 2. When the piston 2 is installed on an upper portion of the mounting hole 11, the piston sealing portion may be positioned above the air passage connection hole 12, so as to isolate the inside of the mounting hole 11 from the outside thereof, so as to be seal and waterproof. When the air nozzle 3 is inserted into the mounting hole 11 to press the piston 2 downward, the piston sealing portion is pressed downward below the vent hole 13 of the air passage 15, so that vent hole 13 of the air passage 15 is exposed to communicate with the air nozzle 3. Whether the piston sealing portion still form a seal with the mounting hole 11 when it is positioned below the vent hole 13 of the air passage 15 is not specifically limited here.

The air nozzle 3 is used to communicate the air bag 4 and the air pump 5, so that the gas output by the air pump 5 enters the air bag 4. The air nozzle 3 has a through hole 35 with one end communicating with the air bag 4, and the other end communicating with the air passage connection hole 12 when the air nozzle 3 presses the piston 2 downward until the piston sealing portion is positioned below the air channel connection hole 12. For the connection method of the air nozzle 3 and the air bag 4, reference may be made to the conventional connection structure of the air nozzle 3 and the air bag 4, which will not be repeated here. According to needs, the air nozzle 3 and the airbag 4 may be connected in a divided structure, or may be fixedly connected directly, or may be in an integrally formed structure.

The casing 1 is also provided with a barometer 6, such as a barometer 6 for detecting air pressure in the air passage connection hole 12, and the blood pressure is measured by detecting changes in the air pressure by the barometer 6. For the specific setting method and measurement principle of the barometer 6, reference may be made to the principle and related structure of a conventional sphygmomanometer, which will not be repeated here.

Figure 5:
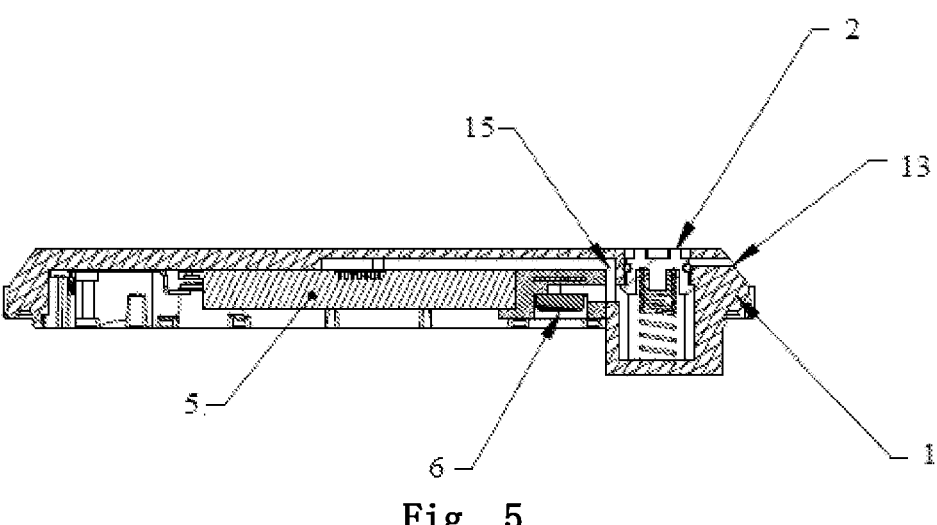
FIG. 5 is a sectional structural schematic view in a state where the air nozzle is not pressed.
Figure 6:
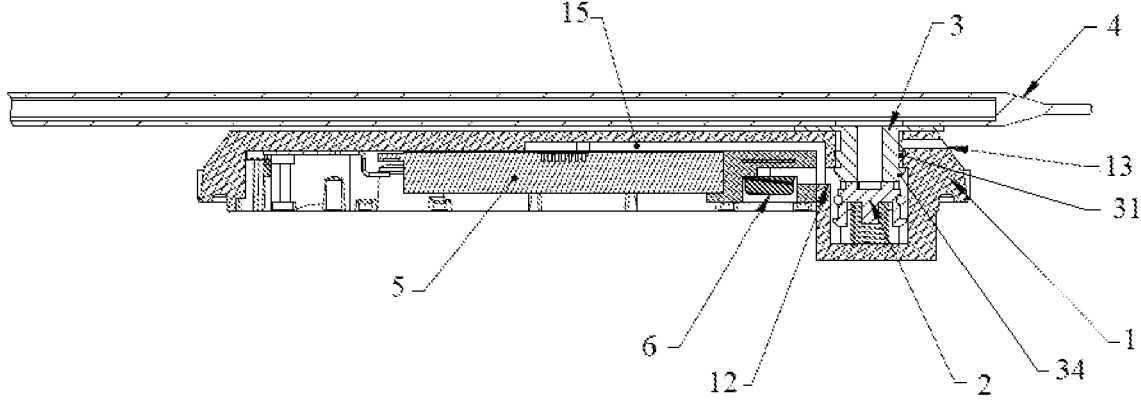
FIG. 6 is a sectional structural schematic view in a state where the air nozzle is pressed.

According to the blood pressure measuring device of the present application, if the blood pressure measurement is not performed, it is not necessary to connect the air nozzle 3 and the air bag 4. Please refer to FIG. 5, the piston is installed on the upper portion of the mounting hole 11, that is, a seal is formed between the piston sealing portion of the piston 2 and the mounting hole 11 positioned above the air passage connection hole 12, thereby achieving a seal between inside and outside of the casing 1, preventing external water from entering the inside the casing 1, thus achieving the purpose of waterproofing. Please refer to FIG. 6, if blood pressure needs to be measured, the air nozzle 3 is pressed into the mounting hole 11 and the air nozzle 3 pushes the piston 2 moving downward, so that the piston sealing portion is positioned below the air passage connection hole 12, and thus the through hole 35 of the air nozzle 3 communicates with the air passage connection hole 12, thereby achieving the communication between the air outlet of the air pump 5 and the air bag 4, for achieving the blood pressure measurement. In conclusion, according the blood pressure measuring device of the present application, by the up and down movement of the piston 2 in the mounting hole 11 and the cooperation of the piston 2 and the air passage connection hole 12, the device body can be waterproof when the airbag 4 is removed in the case that the airbag 4 is not used at ordinary time, and the air nozzle 3 of the airbag 4 is connected if blood pressure needs to be measured, so that the blood pressure can be measured normally.

Specifically, a hook 21 is provided at a bottom end of the piston 2, and a side wall of the mounting hole 11 is provided with a stopper cooperating with the hook 21, to lock the piston sealing portion of the piston 2 above the air passage connection hole 12. Through the cooperation of the hook 21 and the stopper, the position of the piston 2 can be limited in the mounting hole 11 and located at a position where the piston sealing portion is above the air passage connection hole 12. That is, the position of the piston 2 is limited to a position where the inside and outside of the casing of the device are sealed without escaping, without affecting downward movement of the piston 2 under the action of external force.

Further, the mounting hole 11 is a stepped hole including an upper hole and a lower hole with an inner diameter larger than that of the upper hole. The air passage connection hole 12 communicates with the lower hole, and the stopper cooperating with the hook 21 is formed between the upper hole and the lower hole. That is, the mounting hole 11 includes an upper hole and a lower hole, the inner diameter of the upper hole is smaller, and the inner diameter of the lower hole is larger, so that a stepped surface is formed therebetween, and the stepped surface is the above-mentioned stopper, so that the upward movement limit of the stopper is limited when the stopper abuts the hook 21. The air passage connection hole 12 communicates with the lower hole. Thus, on the one hand, when the piston 2 is locked at the upper movement limit position, the sealing can be effectively achieved by the piston sealing portion. Meanwhile, the piston sealing portion can be positioned below the air passage connection hole 12 after the piston 2 moves downward, so as to communicate with the air nozzle 3. In addition, by the arrangement of the stepped hole, there is no need to dispose a separate stopper, and the structure is more compact. In addition, the size of the lower hole is relatively larger, which reduces the resistance of the piston 2 during press-downward, thereby facilitating the air nozzle 3 to press down the piston 2.

In an embodiment, an air nozzle clamper 34 is provided at a bottom end of the air nozzle 3, and a side wall of the mounting hole 11 is provided with an air nozzle stopper cooperating with the air nozzle damper 34 to lock the piston 2 in the mounting hole 11. Through the arrangement of the air nozzle clamper 34 and the air nozzle stopper, after the air nozzle 3 is inserted into the mounting hole 11 and the piston 2 is pressed downward by an external force, the air nozzle 3 can be stably installed in the mounting hole 11 under the engagement of the air nozzle clamper 34 and the air nozzle stopper, and can be kept in the installation position even if the external force is released, so there is no need to keep pressing the valve 3 during blood pressure detection, which is convenient for users to perform detection. Preferably, when the side wall of the mounting hole 11 is provided with a stopper cooperating with the hook 21 of the piston 2, the above-mentioned air nozzle stopper and the stopper cooperating with the hook 21 of the piston 2 are the same component. For example, in a situation that the mounting hole 11 is a stepped hole including an upper hole and a lower hole and a stopper is formed between the upper hole and the lower hole, the hook 21 is an air nozzle stopper. The positions of the air nozzle 3 and the piston 2 are limited by the same structure, which further simplifies the structure.

In an embodiment, a protrusion 22 is formed at a top end of the piston 2. When the air nozzle 3 presses the piston 2 downward, a lower end surface of the air nozzle 3 abuts against the protrusion 22 to form a connection channel communicating with the through hole 35 and allowing gas to pass therethrough between the piston 2 and the air nozzle 3. The protrusion 22 on the top surface of the piston 2 can not only abut against the air nozzle 3, but also a connection channel allowing gas to pass therethrough is formed between the piston 2 and an end surface of the air nozzle 3 by the arrangement of the protrusion 22. Specifically, two protrusions 22 may be provided. For example, protrusions 22 may be provided on opposite sides of the through hole 35 of the corresponding air nozzle 3 and both of the protrusions 22 abut against the end surface of the air nozzle 3. Specially, a lower end surface of the air nozzle 3 may be a flat surface, and the above-mentioned connection channel is formed between the lower end surface of the air nozzle 3 and the top surface of the piston 2. With the above arrangement, the structure is simple, and reliable communication between the through hole 35 of the air nozzle 3 and the air passage connection hole 12 during measurement is ensured. According to needs, the through hole 35 of the air nozzle 3 can also be arranged in a special structure, for example, an L-shaped through hole is provided to communicate with the air passage connection hole 12, but the structure is relatively complex, and there is a relatively high requirement for the angle in circumferential by inserting the air nozzle 3 into the mounting hole 11.

In an embodiment, the piston sealing portion is a sealing ring 23 disposed on an outer wall surface of the piston 2, and a seal is formed between the sealing ring 23 and the side wall of the mounting hole 11. That is, the piston sealing portion adopts the sealing ring 23, which has a simple structure and reliable sealing. Specifically, on the side wall of the piston 2, when the piston 2 is provided with the hook 21, an installation groove is provided on the side wall of the piston 2 at the position above the hook 21, the sealing ring 23 is installed in the installation groove, and a thickness of the sealing ring 23 is greater than a depth of the installation groove, so that the sealing ring 23 can be squeezed between the side wall of the mounting hole 11 and a bottom of the installation groove to form a reliable seal. If the piston 2 is made of rubber, at least a part of the piston 2 may be used as the piston sealing portion.

Figure 7:
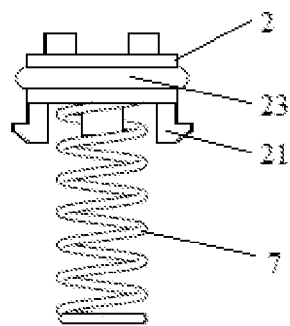
FIG. 7 is a schematic view of the cooperation of the piston and the restoring elastic member.
Figure 8:
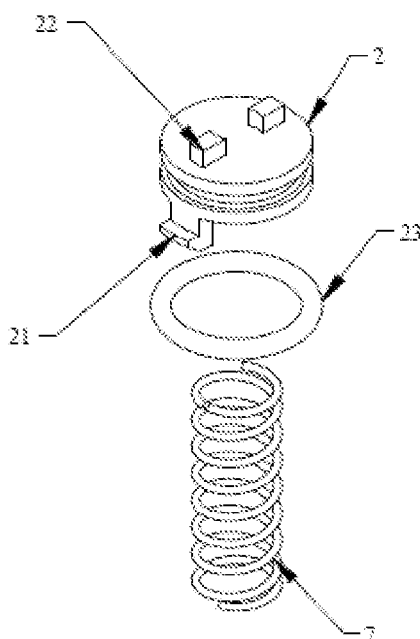
FIG. 8 is an exploded structural schematic view of FIG. 5.

In order to facilitate the restoration of the piston 2 when the air nozzle 3 is removed after the piston 2 moved downward under the installation of the air nozzle 3, please refer to FIGS. 7 and 8. FIG. 7 is a schematic view of the cooperation between the piston and the restoring elastic member; and FIG. 8 is an exploded structural schematic view of FIG. 5. A restoring elastic member 7 is provided to be cooperated with the piston 2, and the restoring elastic member 7 deforms when the piston 2 moves downward relative to the mounting hole 11 to generate a force that pushes the piston 2 to restore to an upper portion of the air passage connection hole 12. That is, when the air nozzle 3 is inserted into the mounting hole 11, it needs to overcome the force of the restoring elastic member 7 as it presses the piston 2 downward, so that the restoring elastic member 7 deforms. After the measurement is completed, the air nozzle 3 is taken out, and the piston 2 is automatically return upward under the action of the restoring elastic member 7. In conclusion, through the arrangement of the restoring elastic member 7, it is further convenient for the user to use, and the user experience is improved. Of course, the restoring elastic member 7 may not be provided as required. In this case, after the air nozzle 3 is taken out, the piston 2 is manually pulled upward until the piston sealing portion is positioned above the air passage connection hole 12 and performing sealing.

Specifically, the restoring elastic member 7 is a compression spring having opposite ends abutting against the bottom surfaces of the piston 2 and the mounting hole 11, respectively. That is, the restoring elastic member 7 adopts a spring, which has a structure to provide a reliable elastic restoring force. According to need, the restoring elastic member 7 can also adopt other material or structural member which can provide restoring force. In order to facilitate the installation of the compression spring, the bottom end of the piston 2 is provided with a spring installation groove, the top end of the compression spring is inserted into the spring installation groove, and the bottom end thereof abuts against the bottom surface of the mounting hole 11. With the arrangement of the spring installation groove, the movement and deformation direction of the spring is restricted to make the deformation of the spring more stable.

Figure 9:
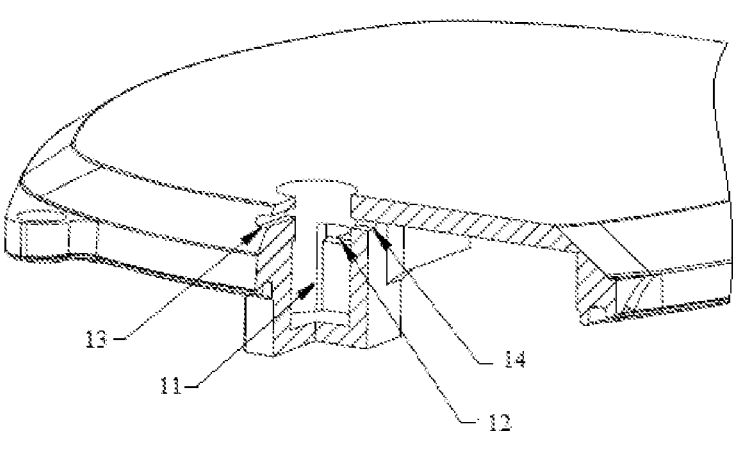
FIG. 9 is a sectional structural schematic view of the casing.
Figure 10:
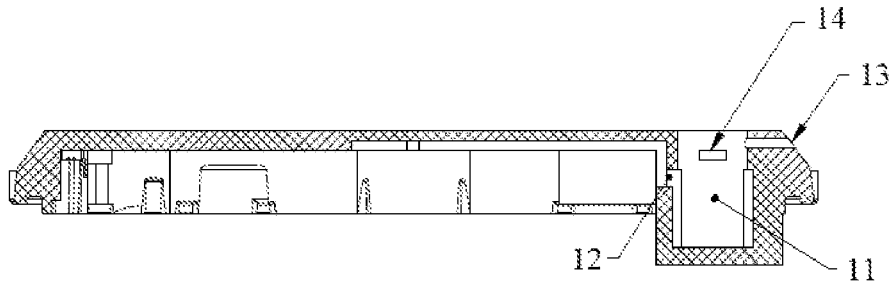
FIG. 10 is a partial sectional view of the casing.

On the basis of the above embodiments, please refer to FIGS. 9 and 10, FIG. 9 is a sectional structural schematic view of the casing and FIG. 10 is a partial sectional view of the casing. The casing 1 is further provided with a vent hole 13 and a pressure relief hole 14. One end of the vent hole 13 communicates with the mounting hole 11, and the other end thereof communicates with the outside of the casing 1. One end of the pressure relief hole 14 communicates with the mounting hole 11, and the other end thereof communicates with an air inlet of the air pump 5. The piston 2 is installed to isolate the vent hole 13 from the pressure relief hole 14 when the piston sealing portion is positioned above the air passage connection hole 12, and the air nozzle 3 communicates the vent hole 13 with the pressure relief hole 14 when the air nozzle 3 presses the piston 2 downward. When the air pump 5 inflates the airbag 4, in order to avoid the negative pressure formed in the casing 1 from affecting the operation of the air pump 5, the vent hole 13 and the pressure relief hole 14 are provided on the casing 1. One end of the vent hole 13 communicates with the mounting hole 11, and the other end thereof communicates to the outside of the casing 1. One end of the pressure relief hole 14 communicates with the mounting hole 11, and the other end thereof communicates with the air inlet of the air pump 5. If the blood pressure measurement is not performed, the piston 2 seals the upper portion of the air passage connection hole 12 in the mounting hole 11. At this time, the piston 2 isolates the vent hole 13 from the pressure relief hole 14, that is, the vent hole 13 and the pressure relief hole 14 are not communicate with each other, achieving the isolation and sealing between the inside and the outside of the casing 1. If performing blood pressure measurement, the air nozzle 3 presses the piston 2 downward until the piston sealing portion is below the air passage connection hole 12. At this time, the air nozzle 3 communicates the vent hole 13 with the pressure relief hole 14 and isolates the pressure relief hole 14 from the air passage connection hole 12. In this case, the air inlet of the air pump 5 can be communicated with the outside of the casing 1 through the pressure relief hole 14 and the vent hole 13, and the air outlet of the air pump 5 communicates with the air bag 4, so that the air pressure inside the casing 1 does not become negative when the air pump 5 operates. When the air pump 5 inflates the air nozzle 3, a normal atmospheric pressure can be obtained, and the air bag 4 can be filled. Through the above-mentioned structural arrangement, the airbag 4 can be filled normally, and the inside and outside of the casing 1 can be effectively sealed when blood pressure measurement is not performed, thereby achieving water-proofing.

Figure 11:
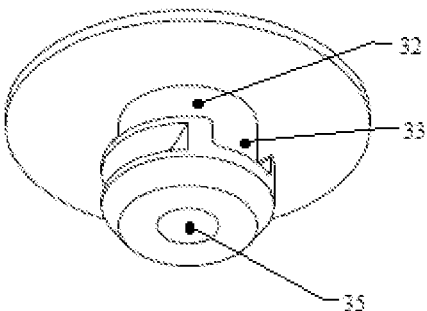
FIG. 11 is a structural schematic view of the air nozzle.

Specifically, please refer to FIGS. 9 to 11, the vent hole 13, the pressure relief hole 14 and the air passage connection hole 12 are disposed in sequence from top to bottom along an axial direction of the mounting hole 11, and the piston 2 can seals the upper portion of the pressure relief hole 14 in the mounting hole 11. The air nozzle 3 includes an air nozzle sealing portion 31 having a bottom end for sealing the side wall of the mounting hole 11 and an annular vent groove 32 positioned above the air nozzle sealing portion 31 and communicating with the vent hole 13. A side of the vent groove 32 facing the pressure relief hole 14 extends downward to form a communication groove 33 that communicates with the pressure relief hole 14. That is, the vent hole 13, the pressure relief hole 14 and the air passage connection hole 12 are formed in sequence from top to bottom along the axial direction of the mounting hole 11. The air nozzle 3 adopts special structural design correspondingly, the bottom portion thereof has an air nozzle sealing portion 31 capable of being sealed connected with the side wall of the mounting hole 11, so as to achieve sealing between inside and outside of the mounting hole 11, and isolating the air passage connection hole 12 from the pressure relief hole 14. The vent groove 32 on the air nozzle 3 faces the vent hole 13 to achieve communication therebetween, so that the external air can enter the vent groove 32 through the vent hole 13. A side of the vent groove 32 facing the pressure relief hole 14 extends downward to form a communication groove 33 communicating with the pressure relief hole 14, so that gas enters the pressure relief hole 14 through the vent groove 32 and the communication groove 33, and then enters the air inlet of the air pump 5. When the air nozzle 3 is taken out, the piston 2 is installed on the upper portion of the mounting hole 11, and the piston sealing portion is positioned above the pressure relief hole 14, so as to isolate the vent hole 13 communicating with the outside from the inside of the casing 1 to achieve effective sealing. In summary, by the height difference between the pressure relief hole 14 and the air passage connection hole 12 and the special structural design of the air nozzle 3, the communication of the pressure relief hole 14 with the vent hole 13 and the isolation from the air passage connection hole 12 is easily realized when the air nozzle 3 is inserted into the mounting hole 11 and the piston 2 is pressed down until the piston sealing portion is positioned below the air passage connection hole 12. According to needs, the piston 2 may also be arranged to seal the pressure relief hole 14, and the air nozzle 3 may be arranged to have a structure of connection channel communicating the pressure relief hole 14 and the vent hole 13. Thus, the above effects can also be achieved.

According to needs, an air inlet communicating with the air inlet of the air pump 5 may also be separately provided on the casing 1, and a waterproof membrane may be arranged on the air inlet. The waterproof membrane can allow gas pass therethrough and performing waterproof. Alternatively, when the internal space of the casing 1 is large enough or the internal air pressure is high enough to satisfy the inflation requirement of the air bag 4, the above-mentioned air intake structure and sealing arrangement may not be performed, that is, it is enough that the air pump 5 uses the internal gas of the casing 1.

In the above embodiments, the device body is a watch body, and the casing 1 is a rear case of the watch body. That is, the blood pressure measuring device is a watch with a blood pressure measurement function, and the rear case is the case 1 on a side that is in contact with the user's wrist when worn. For other structures of the watch, reference may be made to the prior art, which will not be repeated here. Of course, the blood pressure measuring device is not limited to a watch, and may also be other wearable devices such as a wristband, or a portable blood pressure measuring device.

The various embodiments in the present specification are described in a progressive manner, and each embodiment focuses on the differences from other embodiments, and the same and similar parts between the various embodiments can be referred to each other.

The above description of the disclosed embodiments enables any person skilled in the art to implement or make use of the present application. Various modifications to these embodiments will be readily apparent to those skilled in the art, and the generic principles defined herein may be implemented in other embodiments without departing from the spirit or scope of the present application. Therefore, this application is not intended to be limited to the embodiments shown herein, but is to be accorded the widest scope consistent with the principles and novel features disclosed herein.

What is claimed is:

1. A blood pressure measuring device comprising a device body, an air bag, an air nozzle and a piston,
   wherein an air pump is provided in the device body, a mounting hole and an air passage connection hole communicating with the mounting hole are provided on a casing of the device body, and the air passage connection hole is communicated with an air outlet of the air pump,
   wherein the piston is installed in the mounting hole-, and the piston includes a piston sealing portion, to form a seal between the piston sealing portion and a part of the mounting hole positioned above the air passage connection hole, and
   wherein the air nozzle includes a through hole communicating with the air bag, and when the air nozzle is inserted into the mounting hole, the air nozzle presses the piston downward until the piston sealing portion is positioned below the air passage connection hole, and the through hole is communicated with the air passage connection hole,
   wherein the air passage connection hole is in an upper part of the mounting hole and on a side of the mounting hole,
   wherein the blood pressure measuring device further comprises a restoring elastic member cooperating with the piston, and the restoring elastic member deforms when the piston moves downward relative to the mounting hole, so as to generate a force that pushes the piston to restore to an upper portion of the air connection hole.

2. The blood pressure measuring device according to claim 1, wherein a bottom end of the piston is provided with a hook, and a side wall of the mounting hole is provided with a stopper cooperating with the hook, to lock the piston sealing portion of the piston above the air passage connection hole.

3. The blood pressure measuring device according to claim 2, wherein the mounting hole is a stepped hole comprising an upper hole and a lower hole with an inner diameter larger than that of the upper hole, the air passage connection hole is communicated with the lower hole, and the stopper cooperating with the hook is formed between the upper hole and the lower hole.

4. The blood pressure measuring device according to claim 1, wherein a top end of the piston is formed with a protrusion, and when the air nozzle presses the piston downward, a lower end surface of the air nozzle abuts against the protrusion to form a connecting channel communicating with the through hole, allowing gas to pass therethrough between the piston and the air nozzle.

5. The blood pressure measuring device according to claim 1, wherein the piston sealing portion is a sealing ring provided on an outer wall surface of the piston, and a seal is formed between the sealing ring and a side wall of the hole.

6. The blood pressure measuring device according to claim 1, wherein the restoring elastic member is a compression spring having opposite ends abutting against bottom surfaces of the piston and the mounting hole, respectively.

7. The blood pressure measuring device according to claim 1, wherein the casing is further provided with a vent hole having one end communicating with the mounting hole and the other end communicating with an outside of the casing, and a pressure relief hole having one end communicating with the mounting hole and the other end communicating with an air inlet of the air pump, the vent hole isolates from the pressure relief hole when the piston sealing portion of the piston is positioned above the air passage connection hole, and the vent hole is communicated with the pressure relief hole when the air nozzle presses the piston downward.

8. The blood pressure measuring device according to claim 7, wherein the vent hole, the pressure relief hole and the air passage connection hole are disposed sequentially from top to bottom along an axial direction of the mounting hole, wherein the piston seals an upper portion of the pressure relief hole in the mounting hole, and wherein the air nozzle comprises an air nozzle sealing portion having a bottom end for sealing a side wall of the mounting hole and an annular ventilation groove positioned above the air nozzle sealing portion and communicating with the vent hole, a side of the ventilation groove facing the pressure relief hole extends downward to form a communication groove communicating with the pressure relief hole.

9. The blood pressure measuring device according to claim 1, wherein the device body is a watch body, and the casing is a rear case of the watch body.

\* \* \* \* \*